(12) United States Patent
Betts

(10) Patent No.: US 11,826,492 B2
(45) Date of Patent: Nov. 28, 2023

US011826492B2

(54) INTRATUMORAL DRUG DELIVERY MATERIALS AND METHODS FOR TREATING BREAST CANCER

(71) Applicant: BIOTRONIK AG, Buelach (CH)

(72) Inventor: Ronald E. Betts, La Jolla, CA (US)

(73) Assignee: BIOTRONIK AG, Buelach (CH)

( * ) Notice: Subject to any disclaimer, the term of this patent is extended or adjusted under 35 U.S.C. 154(b) by 1021 days.

(21) Appl. No.: 16/465,937

(22) PCT Filed: Dec. 19, 2017

(86) PCT No.: PCT/EP2017/083609
§ 371 (c)(1),
(2) Date: May 31, 2019

(87) PCT Pub. No.: WO2018/114989
PCT Pub. Date: Jun. 28, 2018

(65) Prior Publication Data
US 2020/0030498 A1    Jan. 30, 2020

Related U.S. Application Data

(60) Provisional application No. 62/437,685, filed on Dec. 22, 2016.

(51) Int. Cl.

| | |
|---|---|
| *A61L 29/08* | (2006.01) |
| *A61K 31/337* | (2006.01) |
| *A61K 31/436* | (2006.01) |
| *A61K 31/437* | (2006.01) |
| *A61L 29/16* | (2006.01) |
| *A61L 29/04* | (2006.01) |
| *B05D 1/18* | (2006.01) |
| *A61K 38/38* | (2006.01) |

(52) U.S. Cl.
CPC ............ *A61L 29/08* (2013.01); *A61K 31/337* (2013.01); *A61K 31/436* (2013.01); *A61K 31/437* (2013.01); *A61L 29/048* (2013.01); *A61L 29/085* (2013.01); *A61L 29/16* (2013.01); *A61K 38/385* (2013.01); *A61L 2300/204* (2013.01); *A61L 2300/22* (2013.01); *A61L 2300/426* (2013.01); *A61L 2300/61* (2013.01); *A61L 2300/802* (2013.01); *A61L 2420/00* (2013.01); *A61L 2420/02* (2013.01); *A61L 2420/08* (2013.01); *A61L 2430/04* (2013.01); *B05D 1/18* (2013.01)

(58) Field of Classification Search
None
See application file for complete search history.

(56) References Cited

U.S. PATENT DOCUMENTS

| | | | | |
|---|---|---|---|---|
| 5,286,254 | A * | 2/1994 | Shapland | .......... A61M 37/0092 |
| | | | | 604/20 |
| 9,474,834 | B2 * | 10/2016 | Pacetti | .................... A61L 31/16 |
| 10,525,171 | B2 * | 1/2020 | Ruane | ................... A61L 29/085 |
| 2004/0117007 | A1 * | 6/2004 | Whitbourne | ........... A61L 31/10 |
| | | | | 623/1.42 |
| 2006/0069427 | A1 | 3/2006 | Savage et al. | |
| 2007/0104753 | A1 | 5/2007 | Flanagan | |

FOREIGN PATENT DOCUMENTS

| | | | | |
|---|---|---|---|---|
| EP | 2793967 | | 9/2012 | |
| WO | 2013007653 | | 1/2013 | |
| WO | WO-2013007653 | A1 * | 1/2013 | .......... A61K 31/439 |
| WO | 2013182503 | | 12/2013 | |

* cited by examiner

*Primary Examiner* — Melissa S Mercier
(74) *Attorney, Agent, or Firm* — Lewis Kohn & Walker LLP; David M. Kohn

(57) ABSTRACT

Generally, the invention is in relation to the field of drug delivery devices to augment standard radiation therapy and methods of making and using same. Specifically, this technology utilizes a controlled release of drug from a coated balloon for local intratumoral drug delivery to breast tissue to supplement or replace standard radiation therapy.

14 Claims, 4 Drawing Sheets

Specification includes a Sequence Listing.

SEQUENCE LISTING

<160> NUMBER OF SEQ ID NOS: 1

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
    115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

```
Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```

INTRATUMORAL DRUG DELIVERY MATERIALS AND METHODS FOR TREATING BREAST CANCER

FIELD OF THE INVENTION

This application relates generally to the field of drug delivery devices to augment standard radiation therapy and methods of making and using same. Specifically, this technology utilizes a controlled release of drug from a coated balloon for local intratumoral drug delivery to breast tissue to supplement or replace standard radiation therapy.

BACKGROUND OF THE INVENTION

Breast cancer is the most common form of cancer in women. It is estimated that over 500,000 women die in 2011, worldwide, due to breast cancer (Global Health Estimates, WHO 2013). Although breast cancer is thought to be a disease of the developed world, nearly half of breast cancer cases and 58% of deaths occur in less developed countries (GLOBOCAN 2008). The estimated number of new breast cancer cases among women worldwide in 2012 was 1.7 million. It has been estimated that 1 in 8 women in the US will be diagnosed with some form of breast cancer during their lifetime.

There are several preferred ways for treating breast cancer, depending on the type and stage of the disease: local treatments, systemic treatments and lumpectomies.

Local treatments have been utilized for decades and involve local therapies, including surgery and radiation treatment directed to the diseased tissue.

Systemic treatments involve drugs given orally or intravenously in order to provide entry into the bloodstream.

Lumpectomy is one type of local treatment where the tumor and some normal surrounding tissue is removed. Most patients receive several weeks of radiation therapy post-lumpectomy to eliminate any cancer cells that may still remain in the surrounding tissue. Importantly, two separate studies have shown that 14% of women in one and 9% in the other study, who had lumpectomy plus radiation therapy, resulted in a recurrence confined to that same area (Cao et al., Curr Oncol, 20(6):e593-e601, 2013).

Beginning in 2001 in Europe (and 2002 in the US) a new form of internal, intracavity brachytherapy treatment was approved known as MammoSite®. This new device utilized an insertable, silicone balloon catheter and inflated with saline/contrast solution in order to position the balloon in the cavity which was created when the tumor was removed. (MammoSite® Instruction Manual, Hologic, Inc., Marlborough, MA). The balloon is inflated and a radioactive "seed", which is attached to a guidewire, is advanced into the balloon. The "seed" is removed after a prescribed number of minutes, leaving the balloon in place. This protocol is done twice per day, for five days, after which time the balloon is removed. The advantage of this treatment is that radiation is localized to the site and the course of treatment is shorter than traditional radiation therapy, which can last up to seven weeks.

While initial reports indicated a high success rate for the MammoSite® treatment, more recent studies report various complications when compared to whole breast radiation treatment (WBRT). A 2013 study compared 71 MammoSite® patients with 245 WBRT patients, with both groups being well-matched with respect to clinical characteristics. Median follow-up was 4 years with a palpable mass evidenced at the site of the lumpectomy in 27% of the MammoSite® patients compared to 7% within the WBRT patient group. (p<0.0001). Telangiectasis (lesions formed by a dilated capillary or terminal artery) developed more frequently in the MammoSite® group when compared to the WBRT group (24% vs. 4%, p<0.001), with 42% of patients in the MammoSite® group developing a palpable mass, telangiectasia or both (Kari et al., *J Am Coll Surg*, 217(3), 2013).

In a 54 patient study, the incidence of radiation-induced fat necrosis when using MammoSite® treatment was reported (Paryani et al., *J Contemp Brachytherapy*, 7(1), 2015), It should be noted that WBRT is not without its own set of unique complications, thus evidencing a current need for improved therapies for treating breast cancer.

Previous studies have shown that water-based gelatin (at various concentrations) mimics certain mechanical/chemical properties of breast tissue (Insana et al., *J Mammary Gland Biol Neoplasia*, 9(4):393-404, 2004; Keralapura, Doctoral Dissertation, U California, Davis, 2006). Additionally, cancerous breast tissue has been found to have elevated albumin (~10 gm/mL) content (Etzrodt et al., *Geburtshilfe Frauenheilkd*, 43(11):670-673, 1983).

There is a need in the state of the art to improve patient outcome by either reducing or eliminating radiation exposure by use of a combination of drug plus reduced radiation or localized drug delivery only while retaining the point-of-care advantages associated with the prior art devices without the attendant disadvantages. Additionally, there exists a need for a drug eluting balloon for local intratumoral delivery, where the drug remains on the balloon surface during catheter insertion and is only released once the balloon is inflated or deployed at the target site, with the drug being retained at the target site at a therapeutically effective concentration over a period of time.

SUMMARY OF THE INVENTION

The present invention provides for a drug eluting device, preferably a balloon catheter, comprising a primer drug releasing layer containing a water soluble, preferably neat, material layer and a multi-part drug layer having a first part and optionally a second part, wherein the first part comprises a macrocyclic triene immunosuppressive compound and the second part comprises at least one polymer-free excipient, preferably a nonionic surfactant. The optional polymer-free excipient can be a fatty alcohol, fatty aldehyde or fatty acid or mixtures thereof. In one embodiment the polymer-free excipient is selected from fatty alcohols or fatty aldehydes as defined herein and is preferably selected from fatty alcohols. The polymer-free excipient can further be saturated or unsaturated, linear or branched and is preferably saturated and linear. Optionally, the drug eluting device such as a balloon catheter is comprised of a primer drug releasing layer and a drug layer, wherein the drug layer comprises a macrocyclic triene immunosuppressive compound. Optionally, the drug releasing layer is allowed to dry prior to the application of the drug layer. Preferably, the water soluble material drug releasing layer is globular serum protein and the macrocyclic triene immunosuppressive compound is lipophilic. In a similar aspect, the water soluble material layer is composed of a polymer or a protein having an approximate molecular weight of between 50 to 200 kD. In one embodiment the water soluble material is a polymer or a protein having an approximate molecular weight of between 65-70 kD. In a further embodiment the water soluble material is selected from blood proteins such as globulins and/or fibrinogens having molecular weights up to approximately 160 kD.

In one aspect, the present invention teaches a method of manufacturing a drug eluting device such as a balloon catheter comprising: (a) providing a device, preferably a balloon catheter capable of radial expansion once inflated; (b) providing an aqueous solution of a water soluble agent or excipient preferably comprising from about 10% to about 30% of the water soluble agent or excipient in a solution of water; (c) coating, preferably dip coating the device in the solution of (b); (d) allowing the coated device to dry; (e) applying a solution comprising a macrocyclic triene immunosuppressive compound and optionally at least one polymer-free excipient to the device of (d); and (f) allowing the device of (e) to dry.

In one specific aspect, the present invention teaches a method of manufacturing a drug eluting balloon catheter comprising: (a) providing a balloon catheter capable of radial expansion once inflated; (b) providing an aqueous solution of a water soluble agent preferably comprising from about 10% to about 30% of the water soluble agent in a solution of water; (c) dip coating the balloon catheter in the solution of (b); (d) allowing the dip coated balloon catheter to dry; (e) applying a solution comprising a macrocyclic triene immunosuppressive compound and optionally at least one saturated fatty alcohol polymer-free excipient to the balloon catheter of (d); and (f) allowing the balloon catheter of (e) to dry.

In another aspect, the present invention provides a medical device comprising a catheter with a balloon (balloon catheter) having a primer coating layer comprising a water soluble agent and a second, preferably outermost layer containing optionally a fatty alcohol or fatty aldehyde lipid excipient and a drug, wherein the water soluble agent is a globular serum protein, the fatty alcohol or aldehyde lipid excipient is a nonionic, linear hydrocarbon and the drug is a lipophilic, macrocyclic triene immunosuppressive compound, further wherein the outermost coating layer is capable of forming cracks after the balloon catheter is deployed.

In another aspect, the present invention is related to the use of a non-polymer, saturated or unsaturated fatty alcohol or saturated or unsaturated fatty aldehyde as described herein and preferably having the formula $C_xH_yO$, wherein x is at least 12 and at the most 34, and y is at least 22 and at the most 70 as a coating material for balloon catheters. Further, the present invention is related to the use of multi-part drug solution having at least two parts, wherein the first part comprises or consists of a non-polymer, saturated or unsaturated fatty alcohol or saturated or unsaturated fatty aldehyde as described herein and preferably having the formula $C_xH_yO$, wherein x is at least 12 and at the most 34, and y is at least 22 and at the most 70, and the second part comprises or consists of a drug, preferably a lipophilic, macrocyclic triene immunosuppressive compound as defined herein as a coating material for balloon catheters.

In yet another embodiment, the present invention provides a method of treating breast cancer, comprising (a) providing a drug eluting balloon catheter comprising a primer layer containing a water soluble material and a multi-part drug layer having a first part and optionally a second part; (b) inserting the drug eluting balloon catheter into a diseased breast tissue of an individual, further wherein the first part of the multi-part drug layer comprises a macrocyclic triene immunosuppressive compound and the second part comprises at least one polymer-free excipient, wherein the optional polymer-free excipient is a fatty alcohol or fatty aldehyde or a fatty acid or a nonionic surfactant. In a further embodiment of the method of treating breast cancer the optional polymer excipient is at least one saturated or unsaturated fatty alcohol and or at least one saturated or unsaturated fatty aldehyde.

BRIEF DESCRIPTION OF THE DRAWINGS

The disclosed subject matter contained herein is best described in conjunction with the accompanying drawings, in which.

DETAILED DESCRIPTION OF THE INVENTION

Definitions

Figure 1A:
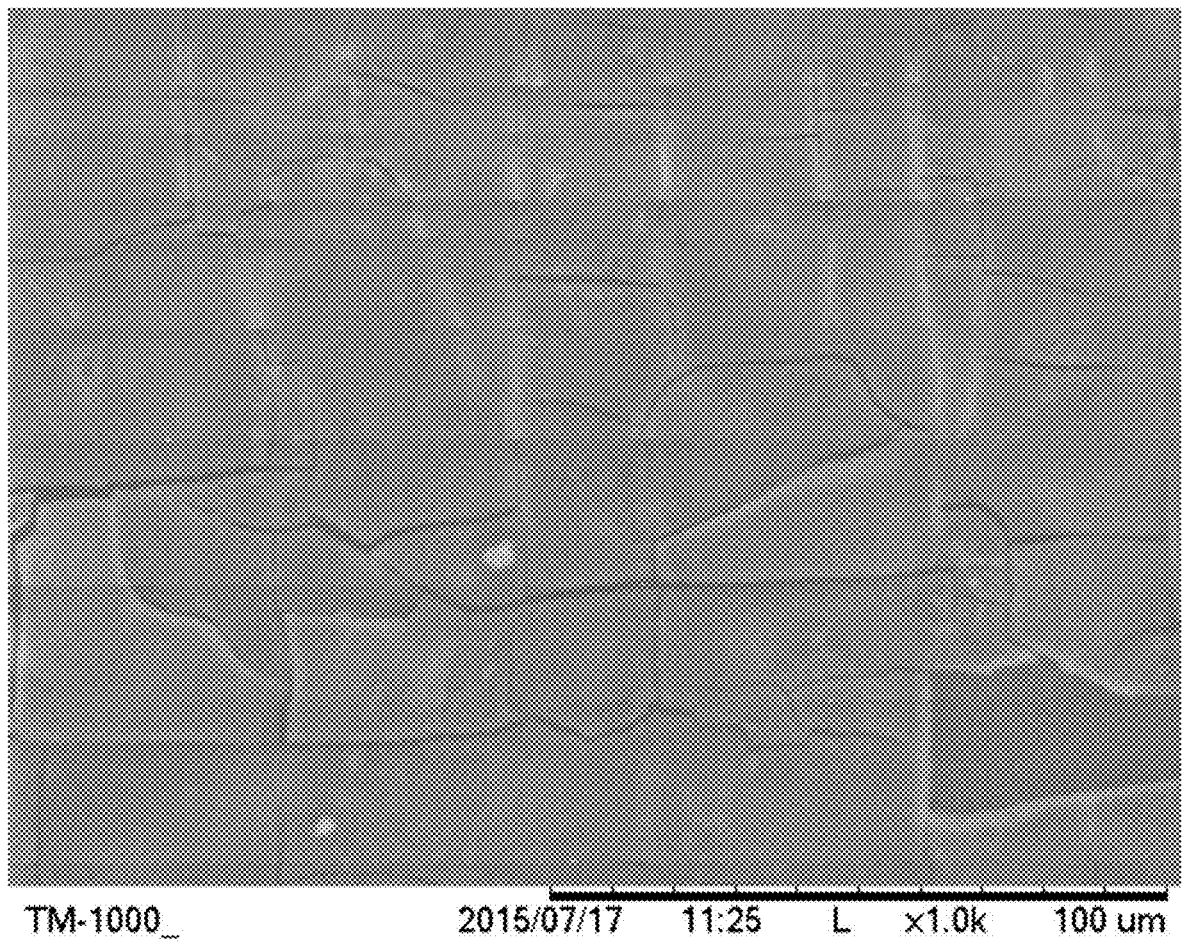
FIG. 1 depicts a photomicrograph evidencing microcracks within the outermost, lipid-drug coating layer after balloon expansion. (A) at 1000× resolution; (B) at 2000× resolution.
Figure 1B:
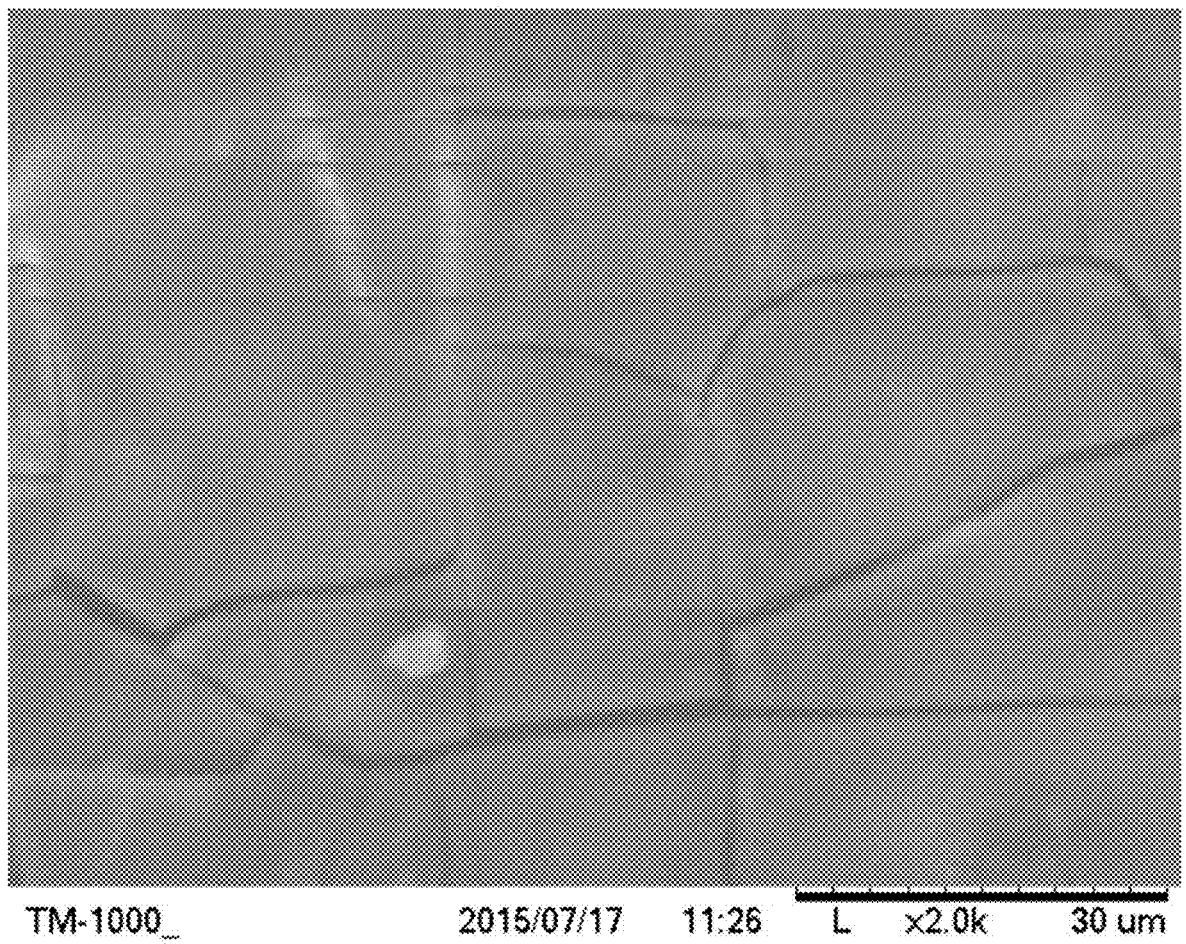

As used herein, the term "coated" or "coating" with reference to a balloon catheter refers to compounds or substances applied to the balloon surface or otherwise integral to the balloon surface. This would include a drug or therapeutic compound, as well as any other substance that is applied to the balloon surface in order to facilitate the delivery of the drug from the balloon surface to a target.

As used herein, the term "elution" refers to the transfer of a drug or therapeutic agent out of the coating layer and is determined as the total amount of the drug or therapeutic agent excreted out of the coating layer as formulated for application to the surface of the balloon catheter of the present invention.

As used herein, the term "excipient" refers to a natural or synthetically derived substance that is formulated in conjunction with an active agent.

As used herein, the term "lipids" refers to any of a group of organic compounds, including the fats, oils, waxes, sterols, and triglycerides, that are largely insoluble in water but soluble in nonpolar organic solvents, and are oily to the touch.

As used herein, the term "target" or "target tissue" refers to the therapeutic endpoint for the devices of the present invention. Such tissues may include, but are not limited to, blood vessels, interior vasculature areas and regions at the interface between organs and the vasculature of an individual.

As used herein, the term macrocyclic triene immunosuppressive compound includes rapamycin (sirolimus), everolimus, zotarolimus, biolimus, novolimus, myolimus, temsirolimus and the rapamycin derivatives described in this disclosure. In one embodiment the macrocyclic triene immunosuppressive compound is selected from the group comprising or consisting of rapamycin (sirolimus), everolimus, zotarolimus and biolimus. Also, the multi-part drug layer may contain tacrolimus, paclitaxel, docetaxel or analogs thereof or mixtures thereof as drug.

The present invention provides for a balloon catheter, and methods of making and using same, having a unique multi-layer coating formulated for application to the external surface of the balloon to be inserted and deployed at the target site. The embodiments of the present invention are designed for insertion into the body of an individual in order to be applied to a target tissue or site of interest. Such non-limiting examples of the application of the devices of the present invention include for use in the treatment of diseases or conditions of the vasculature system, but also include specific targets (i.e., internal organs, certain tissue types or internal regions) that would benefit from the therapeutic uses described herein. In a preferred embodiment, the target tissue is breast tissue and the target site is a solid tumor within the breast tissue. Also, the devices to which the coating as suggested herein can be applied are not limited to balloon catheters, but can also other devices which benefit from a fast and efficient drug release.

It was found that a balloon catheter as suggested herein can be provided which can advantageously be applied in a method of treating breast cancer providing an effective dose of an immunosuppressive compound directly in the affected cancerous tissue in fast manner thereby reducing or in best case eliminating the exposure of a patient to radiation significantly. Hence, a method of treating breast cancer is facilitated which is highly beneficial for the recovery and the long term wellbeing of patients.

The present invention provides for a drug eluting balloon catheter having a coating formulated as follows: a primer layer comprising a water soluble material and a multi-part drug layer, wherein the multi-part drug layer further comprises a macrocyclic triene immunosuppressive compound and optionally at least one fatty alcohol or fatty aldehyde, polymer-free excipient.

Preferably, the primer layer of the multi-layer coating is comprised of a water soluble material and forms the first coating layer on the surface of the balloon catheter. This primer layer is preferably applied via dip coating, wherein the balloon catheter is placed into a solution comprising the water soluble material, which is applied to the surface of the balloon catheter. Other suitable methods such as spraying or application of a solution by a thread, a needle, a cannula, a sponge or a piece of cloth can be used for the coating procedure. Following this application of the primer layer, the balloon catheter is removed from the solution or the application device and allowed to dry, for example at ambient room temperature for a time less than 24 hours The water soluble material that is meant to comprise the bulk of the primer layer is a polymer or a protein having an approximate molecular weight of between 50 to 200 kD. In one embodiment the water soluble material is selected from water soluble human serum proteins or water soluble blood proteins preferably having an approximate molecular weight of between 50 to 200 kD. In one embodiment the water soluble material is a polymer or a protein having an approximate molecular weight of between 65-70 kD, preferably a globular serum protein having an approximate molecular weight of between 65-70 kD. In a further embodiment the water soluble material is selected from blood proteins such as globulins and/or fibrinogens having molecular weights up to approximately 160 kD. More preferably, the water soluble material is human fibrinogen or immunoglobulin. Most preferably, the water soluble material is a human serum protein having at least 90% identity to the following sequence:

(SEQ ID NO: 1)
DARKSEVAHRFKDLGEENFKALVLIAFAQYLQQCPFEDHVKLVNEVTEFA

KTCVADESAENCDKSLHTLFGDKLCTVATLRETYGEMADCCAKQEPERNE

CFLQHKDDNPNLPRLVRPEVDVMCTAFHDNEETFLKKYLYEIARRHPYFY

APELLFFAKRYKAAFTECCQAADKAACLLPKLDELRDEGKASSAKQRLKC

ASLQKFGERAFKAWAVARLSQRFPKAEFAEVSKLVTDLTKVHTECCHGDL

LECADDRADLAKYICENQDSISSKLKECCEKPLLEKSHCIAEVENDEMPA

DLPSLAADFVESKDVCKNYAEAKDVFLGMFLYEYARRHPDYSVVLLLRLA

KTYETTLEKCCAAADPHECYAKVFDEFKPLVEEPQNLIKQNCELFEQLGE

YKFQNALLVRYTKKVPQVSTPTLVEVSRNLGKVGSKCCKHPEAKRMPCAE

DYLSVVLNQLCVLHEKTPVSDRVTKCCTESLVNRRPCFSALEVDETYVPK

-continued

EFNAETFTFHADICTLSEKERQIKKQTALVELVKHKPKATKEQLKAVMDD

FAAFVEKCCKADDKETCFAEEGKKLVAASQAALGL

In a most preferred embodiment of the invention the water soluble excipient is human serum albumin.

Once the primer layer has dried, a multi-part drug layer is applied to the surface of the balloon catheter and on top of the dried primer layer. The multi-part drug layer is formulated to comprise at least two parts, wherein the second part is optional: a first part comprising a drug and optionally a second part comprising a polymer-free excipient as defined herein. In a preferred embodiment, the multi-part drug layer is formulated as a single formulation. In one aspect of the present invention, the drug of the first part of the multi-part drug layer is a macrocyclic triene immunosuppressive compound. More preferably, the drug is a macrocyclic triene immunosuppressive compound having the following structure:

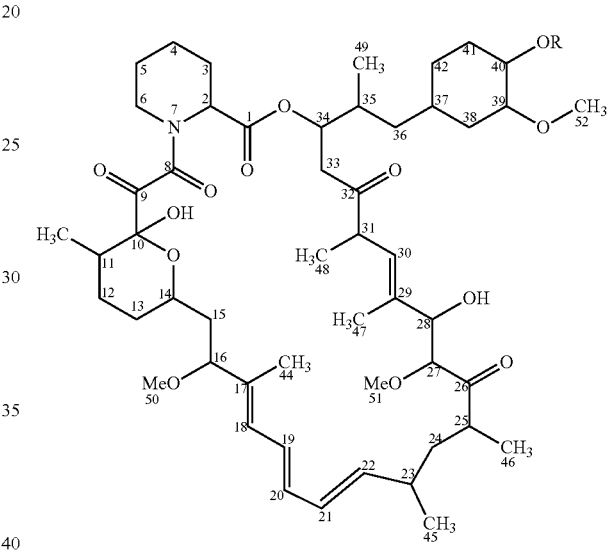

where R is C(O)—(CH$_2$)$_n$—X, n is 0, 1 or 2, X is a cyclic hydrocarbon having 3-8 carbons and optionally contains one or more unsaturated bonds. In a most preferred embodiment, C(O)—(CH$_2$)$_n$—X has one of the following structures:

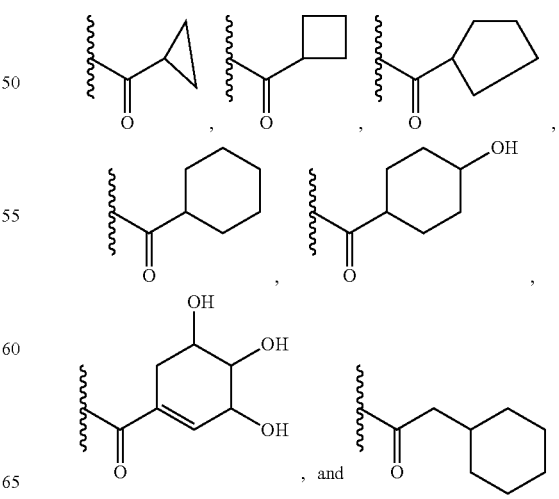

The excipient of the optional second part of the multi-part drug layer is a non-polymer, non-ionic, linear hydrocarbon or surfactant selected from the group consisting of a lipoic fatty alcohol or a fatty aldehyde or a fatty acid or combinations thereof. Preferably, the excipient is a member selected from the group consisting of lauryl alcohol, undecyl alcohol, myristyl alcohol, pentadecyl alcohol, palmitoleyl alcohol, palmityl alcohol, isocetyl alcohol, heptadecanol, lanolin alcohol, stearyl alcohol, isostearly alcohol, 12-hydroxystearyl alcohol, heneicosyl alcohol, behenyl alcohol, erucyl alcohol, 1-tricosanol, lignoceryl alcohol, 1-pentacosanol, ceryl alcohol, 1-heptacosanol, montanyl alcohol, 1-nonacosanol, myricyl alcohol, 1-hentriacontanol, lacceryl alcohol, 1-tritriacontanol, geddyl alcohol, arachidic acid, behenic acid, lignoceric acid and cerotic acid and the like as well as the aldehyde version of each.

Preferably, the fatty alcohol or fatty aldehyde or nonionic surfactant is linear and contains at least 12 carbon atoms. Preferably, the coating comprises a compound having the formula $C_xH_yO$, wherein x is at least 12 and y is at least 22, preferably x is at least 16 and y is at least 28. Yet more preferably, the coating comprises a compound having the formula $C_xH_yO$, wherein x is at least 12 and at the most 34, and y is at least 22 and at the most 70. In one further embodiment, the coating comprises a compound having the formula $C_xH_yO$, wherein x is at least 16 and y is at least 28 and the compound is a non-polymer, linear, branched or cyclic, saturated or unsaturated fatty alcohol or fatty aldehyde. Yet more preferably, the coating comprises a compound having the formula $C_xH_yO$, wherein x is at least 18 and at the most 24, and y is at least 32 and at the most 50, and wherein the compound may further be a non-polymer, linear, branched or cyclic, saturated or unsaturated fatty alcohol or fatty aldehyde, and preferably a linear, saturated fatty alcohol.

In one embodiment, the formulation of the multi-part drug layer comprises at least 80% by weight of the drug as defined herein and at least 15% by weight of at least one polymer-free excipient as defined herein. In a preferred embodiment, the formulation of the multi-part drug layer comprises from 60 to 95% by weight of the drug as defined herein and 5 to 40% by weight of at least one polymer-free excipient as defined. The formulation may further comprise an adequate amount of a solubilizing agent, such as a suitable organic solvent, and particularly a non-polar organic solvent to facilitate suitable application of the formulation such as spray coating. Similarly, the amount of the drug as defined herein applied per drug eluting device, and in particular per balloon catheter is between 5 µg to 25 mg, preferably from about 1 mg to about 10 mg, depending on implant size. The amount of the polymer-free excipient is between 1 µg to 16.7 mg, preferably from about 2 µg to about 2.9 mg. In a most preferred embodiment, the drug load of the drug as defined herein per unit length of the catheter balloon from about 0.5 µg/mm$^2$ to 10 µg/mm$^2$ and preferably from about 1 to 3 µg/mm$^2$.

In a preferred embodiment, the multi-part drug layer comprising the first part and the second part is applied to the surface of the balloon after the primer layer has dried. In a preferred embodiment the multi-part drug layer is applied via spray coating on top of the primer layer. In one aspect, the multi-part drug layer is vacuum dried at a temperature higher than ambient room temperature, preferably in the range of 30 to 50° C. and most preferably at 40° C.

EXAMPLES

Example Formulations

The macrocyclic triene immunosuppressive compound of the present invention has more than one embodiment and may be described as comprising at least one of the following species from Table 1:

TABLE 1

Description of CRC-015 species

| Main structure | R is C(O)—(CH2)n—X having one of the following structures | Species |
|---|---|---|
| (macrocyclic triene structure) | cyclopropyl-C(O)— | CRC-015a |
| | cyclobutyl-C(O)— | CRC-015b |
| | cyclopentyl-C(O)— | CRC-015c |
| | cyclohexyl-C(O)— | CRC-015d |

TABLE 1-continued

Description of CRC-015 species

| Main structure | R is C(O)—(CH2)n—X having one of the following structures | Species |
|---|---|---|
| | cyclohexyl with OH substituent attached via C(O) | CRC-015e |
| | cyclohexenyl with three OH substituents attached via C(O) | CRC-015f |
| | cyclohexyl-CH2-C(O)— | CRC-015g |

CRC-015 is a term meant to encompass a genus and used to refer to each of the following species from Table 1: CRC-015a, CRC-015b, CRC-015c, CRC-015d, CRC-015e, CRC-015f and CRC-015g.

I. Formulation and Coating of Balloon Surface with the Drug Release Layer

Drug Releasing Layer Formulation No. 1:

A solution containing 20% of the water soluble, serum protein in water is prepared. The balloon catheter is dipped into the solution and left for a period of time. The surface-bound releasing agent, known as the primer layer, is allowed to dry at ambient temperature for less than 24 hours.

The serum protein of the primer layer is water soluble and serves a dual purpose of being both a balloon releasing agent (for the drug layer coated thereafter) and a tissue targeting agent. The latter occurs once the balloon is deployed at the target site of interest, where the drug is released through diffusion kinetic effects and specific EPR metabolic features associated with serum protein used in the primer layer.

II. Formulation and Coating of the Balloon Surface with the Multi-Part Drug Layer The multi-part drug layer is formulated to comprise two parts: a first part comprising a drug and a second part comprising a lipid excipient. The drug of the first part of the multi-part drug layer is a macrocyclic triene immunosuppressive compound. The excipient of the second part of the multi-part drug layer is a polymer-free, saturated or unsaturated fatty alcohol or fatty aldehyde. The fatty alcohol as used and described in the present invention is also known as a fatty alcohol modifier.

Specific Examples of Drug Layer Formulation
(Formulation Nos. 1-20)

1. Weigh 6.25 mg 1-hexadecanol (CAS 36653-82-4, Aldrich) into a 10 mL glass vial and add 5 mL acetone. Cap the vial with a PTFE lined cap. Vortex the solution until solids have dissolved. This is labeled as 1.25 mg/mL STOCK 1-hexadecanol. Weigh 6.25 mg CRC-015 into a 3 mL glass vial and add 1 mL STOCK solution. Cap the vial and vortex the solution until solids dissolve. This formulation can be used for device coating.

2. Weigh 6.25 mg 1-octadecanol (CAS 112-92-5, Aldrich) into a 10 mL glass vial and add 5 mL acetone. Cap the vial with a PTFE lined cap. Vortex the solution until solids have dissolved. This is labeled as 1.25 mg/mL STOCK 1-octadecanol. Weigh 6.25 mg CRC-015 into a 3 mL glass vial and add 1 mL STOCK solution. Cap the vial and vortex the solution until solids dissolve. This formulation can be used for device coating.

3. Weigh 6.25 mg 1-hexadecanol into a 10 mL glass vial and add 5 mL chloroform. Cap the vial with a PTFE lined cap. Vortex the solution until solids have dissolved. This is labeled as 1.25 mg/mL STOCK 1-hexadecanol. Weigh 6.25 mg CRC-015 into a 3 mL glass vial and add 1 mL STOCK solution. Cap the vial and vortex the solution until solids dissolve. This formulation can be used for device coating.

4. Weigh 6.25 mg 1-hexadecanol into a 10 mL glass vial and add 5 mL tert-butyl methyl ether. Cap the vial with a PTFE lined cap. Vortex the solution until solids have dissolved. This is labeled as 1.25 mg/mL STOCK 1-hexadecanol. Weigh 6.25 mg CRC-015 into a 3 mL glass vial and add 1 mL STOCK solution. Cap the vial and vortex the solution until solids dissolve. This formulation can be used for device coating.

5. Weigh 6.25 mg 1-hexadecanol into a 10 mL glass vial and add 5 mL 1-chlorobutane. Cap the vial with a PTFE lined cap. Vortex the solution until solids have dissolved. This is labeled as 1.25 mg/mL STOCK 1-hexadecanol. Weigh 6.25 mg CRC-015 into a 3 mL glass vial and add 1 mL STOCK solution. Cap the vial and vortex the solution until solids dissolve. This formulation can be used for device coating.

6. Weigh 6.25 mg 1-docosanol (CAS 30303-65-2 Aldrich) into a 10 mL glass vial and add 5 mL chloroform or 5 mL methyl tert-butyl ether. Cap the vial with a PTFE lined cap. Vortex the solution until solids have dissolved. This is labeled as 1.25 mg/mL STOCK 1-docosanol. Weigh 6.25 mg CRC-015 into a 3 mL glass vial and add 1 mL STOCK solution. Cap the vial and vortex the solution until solids dissolve. This formulation can be used for device coating.
7. Weigh 6.25 mg 1-docosanal (CAS 57402-36-5, Matrix Scientific) into a 10 mL glass vial and add 5 mL chloroform. Cap the vial with a PTFE lined cap. Vortex the solution until solids have dissolved. This is labeled as 1.25 mg/mL STOCK 1-docosanol. Weigh 6.25 mg CRC-015 into a 3 mL glass vial and add 1 mL STOCK solution. Cap the vial and vortex the solution until solids dissolve. This formulation can be used for device coating.
8. Weigh 6.25 mg 1-tetradecanol (CAS 112-72-1, Aldrich) into a 10 mL glass vial and add 5 mL acetone. Cap the vial with a PTFE lined cap. Cap the vial and vortex the solution until solids have dissolved. This is labeled as 1.25 mg/mL STOCK 1-tetradecanol. Weigh 6.25 mg CRC-015 into a 3 mL glass vial and add 1 mL STOCK solution. Cap the vial and vortex the solution until solids dissolve. This formulation can be used for device coating.
9. Weigh 6.25 mg 1-eicosanol (CAS 57402-36-5, TCI) into a 10 mL glass vial and add 5 mL chloroform. Cap the vial with a PTFE lined cap. Vortex the solution until solids have dissolved. This is labeled as 1.25 mg/mL STOCK 1-eicosanol. Weigh 6.25 mg CRC-015 into a 3 mL glass vial and add 1 mL STOCK solution. Cap the vial and vortex the solution until solids dissolve. This formulation can be used for device coating.
10. Weigh 6.25 mg 1-hexadecanol into a 10 mL glass vial and add 5 mL acetone. Cap the vial with a PTFE lined cap. Vortex the solution until solids have dissolved. This is labeled as 1.25 mg/mL STOCK 1-hexadecanol. Weigh 6.25 mg everolimus into a 3 mL glass vial and add 1 mL STOCK solution. Cap the vial and vortex the solution until solids dissolve. This formulation can be used for device coating.
11. Weigh 6.25 mg 1-hexadecanol into a 10 mL glass vial and add 5 mL acetone. Cap the vial with a PTFE lined cap. Vortex the solution until solids have dissolved. This is labeled as 1.25 mg/mL STOCK 1-hexadecanol. Weigh 6.25 mg sirolimus into a 3 mL glass vial and add 1 mL STOCK solution. Cap the vial and vortex the solution until solids dissolve. This formulation can be used for device coating.
12. Weigh 6.25 mg 1-hexadecanol into a 10 mL glass vial and add 5 mL acetone. Cap the vial with a PTFE lined cap. Vortex the solution until solids have dissolved. This is labeled as 1.25 mg/mL STOCK 1-hexadecanol. Weigh 6.25 mg biolimus into a 3 mL glass vial and add 1 mL STOCK solution. Cap the vial and vortex the solution until solids dissolve. This formulation can be used for device coating.
13. Weigh 6.25 mg 1-docosanol into a 10 mL glass vial and add 5 mL acetone. Cap the vial with a PTFE lined cap. Vortex the solution until solids have dissolved. This is labeled as 1.25 mg/mL STOCK 1-docosanol. Weigh 6.25 mg sirolimus into a 3 mL glass vial and add 1 mL STOCK solution. Cap the vial and vortex the solution until solids dissolve. This formulation can be used for device coating.
14. Weigh 6.25 mg 1-tetradecanol into a 10 mL glass vial and add 5 mL acetone. Cap the vial with a PTFE lined cap. Vortex the solution until solids have dissolved. This is labeled as 1.25 mg/mL STOCK 1-tetradecanol. Weigh 6.25 mg zotarolimus into a 3 mL glass vial and add 1 mL STOCK solution. Cap the vial and vortex the solution until solids dissolve. This formulation can be used for device coating.
15. Weigh 6.25 mg 1-hexadecanol into a 10 mL glass vial and add 5 mL acetone. Cap the vial with a PTFE lined cap. Vortex the solution until solids have dissolved. This is labeled as 1.25 mg/mL STOCK 1-hexadecanol. Weigh 6.25 mg paclitaxel into a 3 mL glass vial and add 1 mL STOCK solution. Cap the vial and vortex the solution until solids dissolve. This formulation can be used for device coating.
16. Weigh 12.50 mg 1-octadecanol into a 10 mL glass vial and add 5 mL acetone. Cap the vial with a PTFE lined cap. Vortex the solution until solids have dissolved. This is labeled as 2.5 mg/mL STOCK 1-octadecanol. Weigh 6.25 mg CRC-015 into a 3 mL glass vial and add 1 mL STOCK solution. Cap the vial and vortex the solution until solids dissolve. This formulation can be used for device coating.
17. Weigh 12.50 mg pentadecanol into a 10 mL glass vial and add 5 mL chloroform. Cap the vial with a PTFE lined cap. Vortex the solution until solids have dissolved. This is labeled as 2.5 mg/mL STOCK pentadecanol. Weigh 6.25 mg CRC-015 into a 3 mL glass vial and add 1 mL STOCK solution. Cap the vial and vortex the solution until solids dissolve. This formulation can be used for device coating.
18. Weigh 6.25 mg 1-triacontanol (CAS 593-50-0, Aldrich) into a 10 mL glass vial and add 5 mL chloroform. Cap the vial with a PTFE lined cap. Vortex the solution until solids have dissolved. This is labeled as 1.25 mg/mL STOCK 1-triacontanol. Weigh 6.25 mg docetaxel into a 3 mL glass vial and add 1 mL STOCK solution. Cap the vial and vortex the solution until solids dissolve. This formulation can be used for device coating.
19. Weigh 6.25 mg 12-hydroxystearyl alcohol (CAS 2726-73-0, Aldrich) into a 10 mL glass vial and add 5 mL tert-butyl methyl ether. Cap the vial with a PTFE lined cap. Vortex the solution until solids have dissolved. This is labeled as 1.25 mg/mL STOCK 12-hydroxystearyl. Weigh 6.25 mg sirolimus into a 3 mL glass vial and add 1 mL STOCK solution. Cap the vial and vortex the solution until solids dissolve. This formulation can be used for device coating.
20. Weigh 6.25 mg oleyl alcohol (CAS 143-28-2, Aldrich) into a 10 mL glass vial and add 5 mL chloroform. Cap the vial with a PTFE lined cap. Vortex the solution until solids have dissolved. This is labeled as 1.25 mg/mL STOCK oleyl alcohol. Weigh 6.25 mg paclitaxel into a 3 mL glass vial and add 1 mL STOCK solution. Cap the vial and vortex the solution until solids dissolve. This formulation can be used for device coating.

The specific macrocylic triene immunosuppressive compound, known herein as CRC015, was formulated with the polymer-free excipient and directly applied, via spray coating, onto the surface of the balloon catheter having the primer layer already applied. A solubilizing agent was used in order to make the saturated fatty alcohol readily soluble and to accommodate the formulation with CRC015 prior to spray coating.

The balloon catheter, now having the multi-part drug layer spray coated on top of the primer layer, is dried at 40° in vacuum.

III. Drug Delivery and Transfer Mechanism of CRC015-Coated Balloon for Assessing In Vivo Tissue Uptake During preclinical testing, it was found that CRC015 will bind at high levels with the serum protein of the primer layer (SEQ ID NO: 1) in vivo. It was also discovered that while the serum protein of the primer layer is highly water soluble, CRC015 is highly lipophilic. Accordingly, studies were performed that evidenced the protective properties of CRC015 on the degradative effects on the primer layer during device delivery.

Once the balloon catheter has reached the target tissue, it is deployed or inflated, causing the balloon surface to come in physical contact with the target tissue. After the balloon is deployed, the multi-part drug layer cracks, allowing the infiltration of water molecules in the plasma to interact with the primer layer, which then disassociates from the balloon surface, carrying the bound drug directly into the target tissue, where it continues to elute at a therapeutic rate over extended time.

In vivo drug uptake and retention of drug using the present invention is demonstrated using female hypercholestermic White New Zealand rabbits. To induce atherosclerotic lesions the rabbits were fed a 1% cholesterol plus 6% peanut oil diet (BioServ, Fleming, NJ product F4366). The efficacy of this type of diet on the induction of rabbit hypercholestermia and utility of this model for comparison to human pathogenesis is well validated (Schwartz et al., *J. Am. Coll. Cardiol.* 44(7):1373-1385 (2004)). PTCA balloon catheters (3.0 mm in diameter and 22.9 mm in length) were inflated at 1-3 atm and dip coated with drug releasing formulation No. 1 containing human serum albumin (Sigma A9731) and allowed to dry at ambient temperatures for 24 hours. The albumin coated balloon was then spray coated with drug layer formulation No. 6 and then pleated, folded and heat set at 50 degrees C. for 5 minutes. The folded balloon was then additionally spray coated with formulation No. 6 to achieve a drug dose of 5.75 $\mu g/mm^2$. The drug coated balloon was vacuum dried at 40 degrees C. for 72 hours before use. The endothelial denudation of the rabbits was conducted by a surgical cutdown on the carotid artery and a 4 F hemostatic sheath advanced around the aortic arch. A guide wire was advanced to the femoral artery and a 3.0×10 mm balloon catheter advanced to the distal iliac artery and inflated. The catheter was pulled proximally to the aortoiliac bifurcation and then deflated. This technique was repeated two additional times. This same technique was also conducted to the contralateral iliac artery. The recovered animals were then fed the custom rabbit diet for 42 days. At the end of this time period the prepared drug coated balloons were advanced in each of the treated iliac arteries and inflated to nominal pressure for 60 seconds before removal. The vessels were harvested after 8 days for drug measurement by LCMS after extraction of tissue at balloon treatment site using acetonitrile. Results are presented below at Table 2.

TABLE 2

Assessment of In Vivo Uptake of CRC-015

| Animal | Artery | Drug remaining in vessel after 8 days |
| --- | --- | --- |
| 1 | Right Iliac | 428 ng/mg tissue |
| 2 | Left Iliac | 1326 ng/mg tissue |

Tissue level concentrations after 8 days are significant and demonstrate utility of this invention.

Further comparative studies were performed based on the above in vivo uptake assessment (Study No. 1). Specifically, another study was conducted (Study No. 2) based on Study No. 1, except that normal White New Zealand rabbits were used and the drug dose was reduced to 2.79 $\mu g/mm^2$. Additionally, a final study (Study No. 3) was performed similar to Study No. 1, except normal White New Zealand rabbits were used and drug layer Formulation No. 1 was utilized at a dosing of 2.89 $\mu g/mm^2$. The results of the comparative study are presented below at Table 3.

TABLE 3

Comparative In Vivo Uptake Studies

| Study No. | Vessel Type | Number of Days | Number of Vessels | Normalized Uptake[1] (ng/mg/µg) |
| --- | --- | --- | --- | --- |
| 1 | Rabbit Iliac Arteries | 8 | 2 | 0.73 |
| 2 | Rabbit Iliac Arteries | 8 | 5 | 0.66 |
| 3 | Rabbit Iliac Arteries | 8 | 4 | 0.79 |
| MagicTouch Sirolimus[2] | Rabbit Iliac Arteries | 8 | NA | 0.09 |
| US 2014/0046254 Everolimus | Porcine Coronary Arteries | 3 | NA | 0.02 |
| US 2014/0046254 Zotarolimus | Porcine Coronary Arteries | 7 | NA | 0.04 |

[1]Normalized Uptake as a function of ng drug/mg tissue/µg drug on balloon
[2]Concept Medical, Cardiovascular Innovation Pipeline @ EuroPCR, 26 May 2010.
NA: Data not available As is evidenced in Table 3, the uptake of drug into the target tissues by the devices of the present invention is increased nearly 8-fold when compared to the devices of the current state of the art.

IV. Albumin Binding of Sirolimus (Rapamycin)

Sirolimus-albumin binding has previously been reported. (Rapamune Product Insert) To determine if CRC-015 is bound to albumin and to compare CRC-015 to sirolimus binding characteristics, 1.485 mL samples containing 1.4 mg/mL bovine serum albumin (BSA) in normal saline were spiked with 15 uL of either CRC-015 or sirolimus dissolved in acetonitrile to yield final drug concentrations of 10 uM. The drug spiked BSA solutions were mixed by inversion and allowed to equilibrate at ambient temperature for 30 minutes to allow drug binding to the albumin protein. 826 mg ammonium sulfate was next added to each sample and mixed by gentle inversion until the salt had completely dissolved and precipitate formed. Samples were then vortexed for 20 seconds then centrifuged for 6.5 minutes at 7200×g. To both supernatant and separated precipitate 0.750 mL methanol and 0.250 mL acetonitrile containing internal standard was added to each sample. Samples were tested for drug content by LCMS where the supernatant amount represents unbound drug and the precipitate amount the bound drug. Recovery verification tests were performed as above but using solutions of saline plus drug without BSA.

A summary of the percent unbound and bound of CRC-015 or sirolimus are listed below at Table 4. Values reported are the average of a separate test on each of four separate days.

TABLE 4

Binding Comparison between CRC-015 and Sirolimus

| Drug | % Unbound | % Bound |
| --- | --- | --- |
| CRC-015 | 3.0% | 97.0% |
| Sirolimus | 6.2% | 93.8% |

CRC-015 was determined to have higher binding to albumin. High sirolimus-albumin binding is consistent with previous referenced results.

V. Comparison of Coating Techniques

The coating methods of the present invention, along with the specialized compounds related thereto, are distinguishable over the present state of the art in drug coated medical devices, namely, catheters. A major technical advantage of this new approach, relative to the current state of the art, is the requirement that the therapeutic material is retained on the balloon surface during placement of the catheter, while simultaneously releasing the therapeutic material at the targeted site.

Figure 2A:
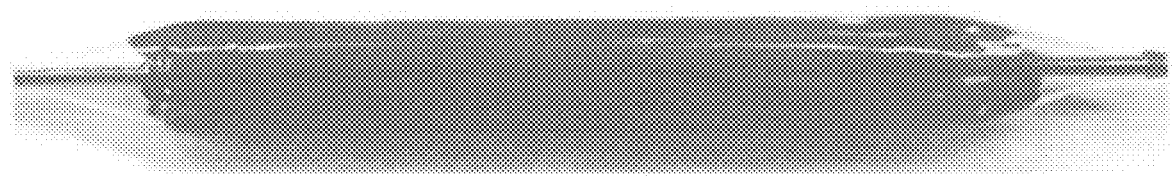
FIG. 2 shows two catheters each containing a nylon balloon and coated with a lipophilic blue dye. (A) Catheter A contained a nylon balloon coated with a lipophilic blue dye simulating the drug embodiment of the present invention; (B) Catheter B contained a nylon balloon first coated with human serum albumin followed by the same amount of lipophilic blue dye as in Catheter A.
Figure 2B:
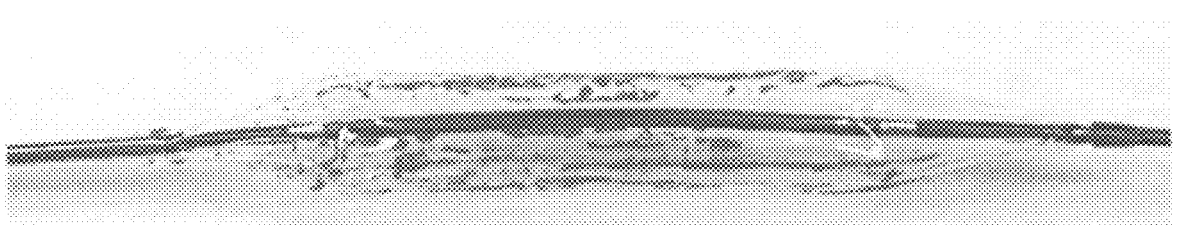

FIG. 2 exemplifies the difference between the present invention and the current state of the art with respect to catheters and drug coated balloons. Catheter A contains a nylon balloon coated with a lipophilic blue dye, designed to mimic the CRC-015 compound (FIG. 2A). Catheter B was a similar balloon to that used in Catheter A, but was first coated with a releasing layer comprised of human serum albumin, followed by the same amount of blue dye used on Catheter A (FIG. 2B). Both balloons were expanded while suspended in a static 0.9% NaCl solution. Catheter B was removed from the solution after 30 minutes while Catheter A was allowed to soak for 24 hours. Catheter B releasing layer proved very effective in causing prompt release of the hydrophobic material, as evidenced in FIG. 2B.

VI. Comparison of Drug Release Profiles

Phosphate buffered saline solutions containing 10 mg/mL human albumin and preserved with 0.1% sodium azide were prepared with either 5.5% (low density tissue) or 50% (very high density tissue) gelatin. Additionally, these solutions were saturated with 1-octanol (2.5 mg/mL) to simulate the breast tissue lipid fraction. For each balloon test, 4 mL of releasing medium was contained in a 5 mL glass test tube. Balloons were prepared by dip coating the releasing layer with drying, followed by coating a 2 mg drug layer from acetonitrile. Releasing media and inflated balloons were maintained at 37° C. during the test. The results of the four balloon test (Studies A-D) are reproduced below in Table 5.

Figure 3:
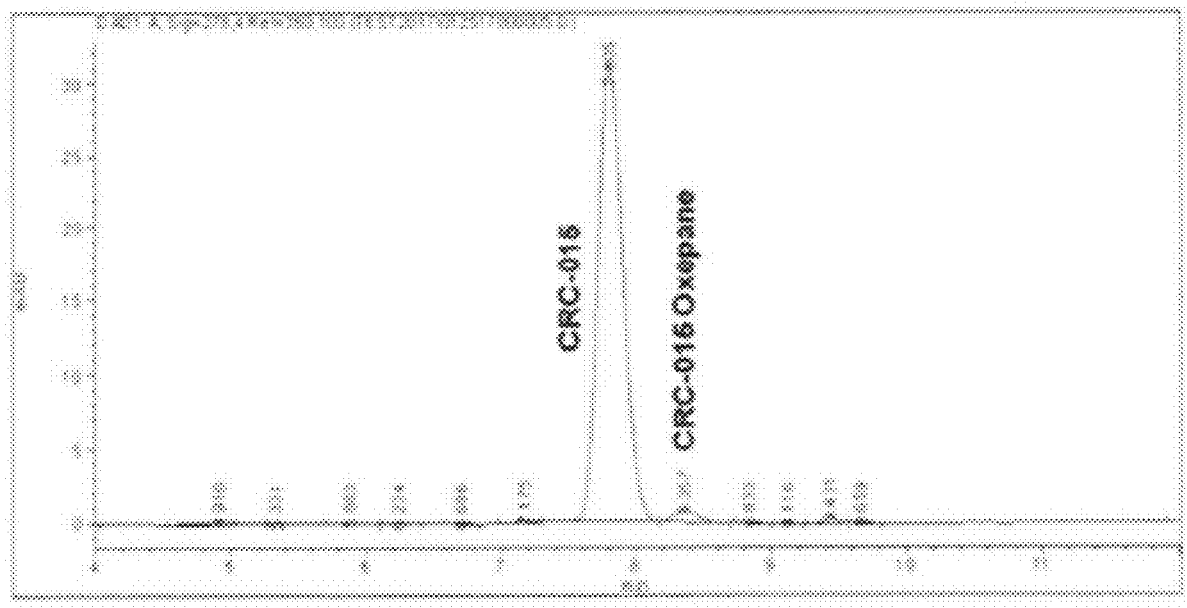
FIG. 3 shows a typical HPLC chromatogram from medium extracted with ethyl acetate confirming an expected drug release profile.

The balloons were placed into the release medium, inflated and allowed to incubate for drug release analysis. Balloons in Studies A and B were allowed to incubate 1 hour while balloons in Studies C and D were allowed 18 hours of incubation time. Balloons were then removed from the medium, extracted with acetonitrile and the adhering drug content was further measured by HPLC. To verify drug release, a semi-quantitative test of each medium was employed, with the in vitro results of that study showing clear and reproducible drug release profile trends (Table 5). Similarly, HPLC chromatogram data show the drug release from the balloon, with ethyl acetate extraction (FIG. 3).

The data of table 5 shows that fast and efficient drug release into even thick breast tissue can be achieved using balloon catheters as suggested herein. Further, it can be extracted from the presented data that the polymer-free excipient can be used to fine tune the drug release from the balloon. Using the polymer-free excipient as suggested herein facilitates sustained released to tissue of the drug after release from the balloon if that is needed for the treating.

TABLE 5

Drug Release Profiles using Nylon or MammoSite ® Device

| | Description | Amount of CRC-015 Recovered from Balloon (µg)/(%) | Amount of CRC-015 released from 2 mg load on the balloon (µg)/(%) |
|---|---|---|---|
| Study A | 5.5% Gelatin | 101 (5.1) | 1899 (94.9) |
| | 5.5% Gelatin | 40 (2.0) | 1960 (98) |

TABLE 5-continued

Drug Release Profiles using Nylon or MammoSite ® Device

| | Description | Amount of CRC-015 Recovered from Balloon (µg)/(%) | Amount of CRC-015 released from 2 mg load on the balloon (µg)/(%) |
|---|---|---|---|
| Study B | 50% Gelatin | 459 (23.0) | 1541 (77) |
| | 50% Gelatin | 332 (16.6) | 1668 (83.4) |
| Study C | MammoSite ® minus FA* | 179 (9.0) | 1821 (91) |
| Study D | MammoSite ® plus FA | 903 (45.2) | 1097 (54.8) |

*FA = fatty alcohol modifier

Balloons in Studies A and B used nylon coronary balloons while Studies C and D utilized MammoSite® silicon balloon catheters. In studies A and B no fatty alcohol was used. The catheter in Study D had a fatty alcohol modifier (FA) added to the drug layer. It is believed this modifier may have the ability to further modify or tune the drug release properties or modify drug tissue uptake and kinetics.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of ordinary skill in the art upon reviewing the above description. The scope of the invention should, therefore, be determined not with reference to the above description, but should instead be determined with reference to the appended claims, along with the full scope of equivalents to which such claims are entitled. The disclosures of all articles and references, including patent publications, are incorporated herein by reference.

It will be apparent to those skilled in the art that numerous modifications and variations of the described examples and embodiments are possible in light of the above teaching. The disclosed examples and embodiments may include some or all of the features disclosed herein. Therefore, it is the intent to cover all such modifications and alternate embodiments as may come within the true scope of this invention.

What is claimed is:

1. A drug eluting device, comprising a primer layer containing a water soluble material layer and a multi-part drug layer having a first part and optionally a second part, wherein the first part comprises a macrocyclic triene immunosuppressive compound and the second part comprises at least one polymer-free excipient, wherein polymer-free excipient is a fatty alcohol or fatty aldehyde or a fatty acid or a nonionic surfactant, wherein the drug eluting device is a drug eluting balloon catheter and wherein the multi-part drug layer is formulated as a single formulation and is applied to the surface of the balloon catheter and on top of the primer layer and wherein the water soluble material is a globular serum protein having an approximate molecular weight of between 65-70 kD.

2. The device of claim 1, wherein the water soluble material comprises a serum protein having at least 90% identity to SEQ ID NO: 1.

3. The device of claim 1, wherein the water soluble material is human serum albumin.

4. The device of claim 1, wherein the multi-part drug layer contains one of rapamycin, everolimus, zotarolimus, biolimus or temsirolimus.

5. The device of claim 1, wherein the multi-part drug layer contains one of tacrolimus, paclitaxel, docetaxel, analogs thereof or mixtures thereof.

6. The device of claim 1, wherein polymer-free excipient is a linear fatty alcohol or fatty aldehyde or a fatty acid or a nonionic surfactant containing at least 12 carbon atoms.

7. The device of claim 1, wherein polymer-free excipient of the second part of the multi-part drug layer is at least one saturated or unsaturated fatty alcohol and/or at least one saturated or unsaturated fatty aldehyde.

8. A method of manufacturing the drug eluting balloon catheter of claim 1 comprising: (a) providing the drug eluting balloon catheter capable of radial expansion once inflated; (b) providing an aqueous solution of a water soluble excipient comprising from about 10% to about 30% of the water soluble excipient in a solution of water; (c) dip coating the drug eluting balloon catheter in the solution of (b); (d) allowing the dip coated drug eluting balloon catheter to dry; (e) applying a solution comprising a macrocyclic triene immunosuppressive compound and optionally at least one saturated fatty alcohol, polymer-free excipient to the drug eluting balloon catheter of (d); and (f) allowing the drug eluting balloon catheter of (e) to dry.

9. A drug eluting device, comprising a primer layer containing a water soluble material layer and a multi-part drug layer having a first part and optionally a second part, wherein the first part comprises a macrocyclic triene immunosuppressive compound and the second part comprises at least one polymer-free excipient, wherein the drug eluting device is a drug eluting balloon catheter and wherein the multi-part drug layer is formulated as a single formulation and is applied to the surface of the balloon catheter and on top of the primer layer, wherein the water soluble material is a globular serum protein, the at least one polymer-free excipient is a fatty alcohol excipient being a nonionic, linear hydrocarbon and the macrocyclic triene immunosuppressive compound is lipophilic, further wherein the coating layer is capable of forming cracks after the device is deployed.

10. A method of treating breast cancer, comprising (a) providing a drug eluting balloon catheter comprising a primer layer containing a water soluble material and a multi-part drug layer having a first part and optionally a second part; (b) inserting the drug eluting balloon catheter into a diseased breast tissue of an individual, further wherein the first part of the multi-part drug layer comprises a macrocyclic triene immunosuppressive compound, wherein the macrocyclic triene immunosuppressive compound has the following structure:

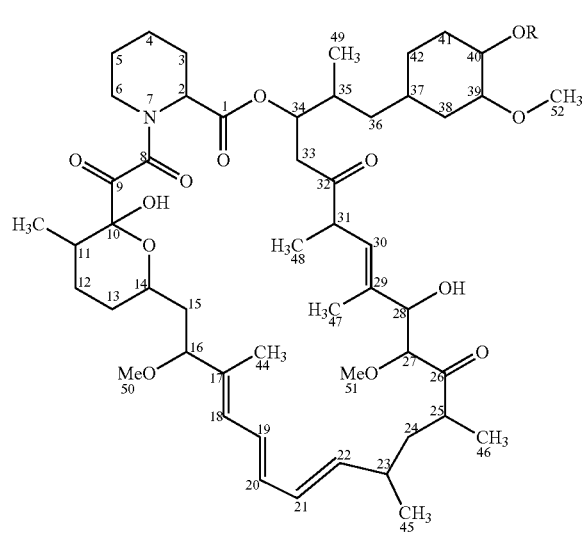

where R is C(O)—(CH$_2$)$_n$—X, n is 0, 1 or 2, X is a cyclic hydrocarbon having 3-8 carbons and optionally contains one or more unsaturated bonds and the optional second part comprises at least one polymer-free excipient, wherein polymer-free excipient is a fatty alcohol or fatty aldehyde or a fatty acid or a nonionic surfactant.

11. The device of claim 1, wherein the macrocyclic triene immunosuppressive compound has the following structure:

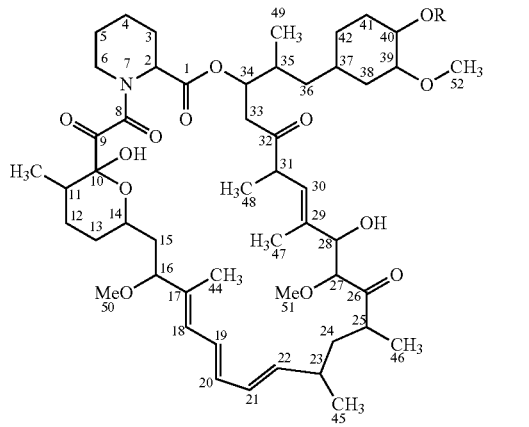

where R is C(O)—(CH$_2$)$_n$—X, n is 0, 1 or 2, X is a cyclic hydrocarbon having 3-8 carbons and optionally contains one or more unsaturated bonds.

12. The device of claim 11, wherein C(O)—(CH$_2$)$_n$—X has one of the following structures:

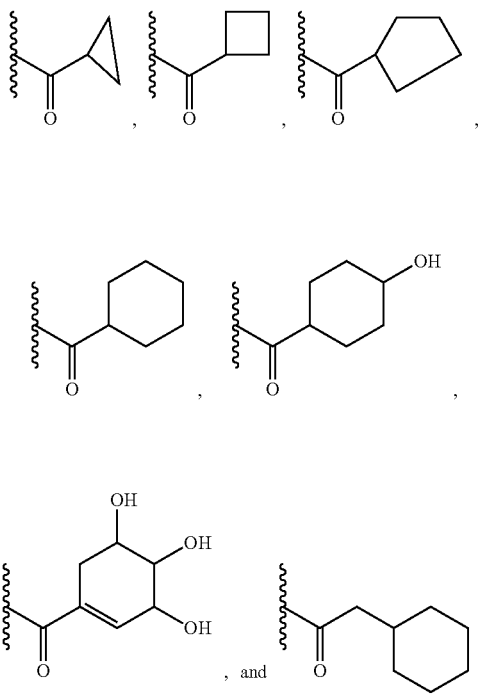

, and

13. The drug eluting device of claim 10, wherein the macrocyclic triene immunosuppressive compound has the following structure:

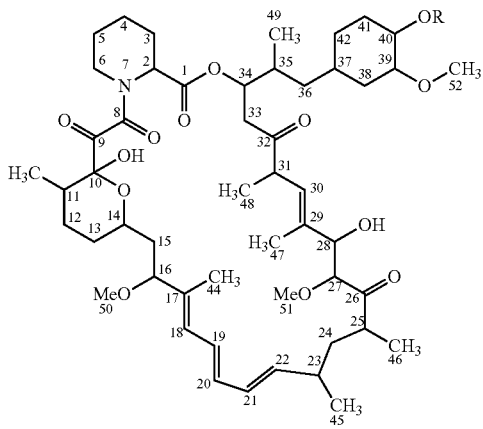

where R is C(O)—(CH$_2$)$_n$—X, n is 0, 1 or 2, X is a cyclic hydrocarbon having 3-8 carbons and optionally contains one or more unsaturated bonds.

14. A drug eluting device, comprising a primer layer containing a water soluble material layer and a multi-part drug layer having a first part and optionally a second part, wherein the first part comprises a macrocyclic triene immunosuppressive compound and the second part comprises at least one polymer-free excipient, wherein polymer-free excipient is a fatty alcohol or fatty aldehyde or a fatty acid or a nonionic surfactant, wherein the drug eluting device is a drug eluting balloon catheter and wherein the multi-part drug layer is formulated as a single formulation and is applied to the surface of the balloon catheter and on top of the primer layer, wherein the water soluble material is a globular serum protein and wherein the macrocyclic triene immunosuppressive compound has the following structure:

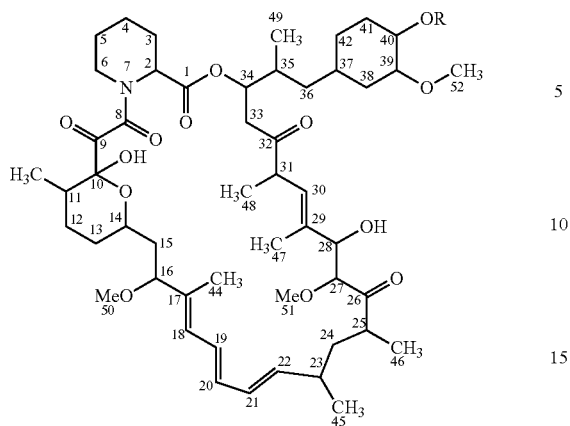
where R is C(O)—(CH$_2$)$_n$—X, n is 0, 1 or 2, X is a cyclic hydrocarbon having 3-8 carbons and optionally contains one or more unsaturated bonds.
* * * * *